(12) United States Patent
Hochstein et al.

(10) Patent No.: US 7,485,183 B2
(45) Date of Patent: Feb. 3, 2009

(54) PIGMENT MIXTURE, AND THE USE THEREOF IN COSMETICS AND IN THE FOODS AND PHARMACEUTICALS SECTOR

(75) Inventors: Veronika Hochstein, Bruchsal (DE); Sabine Schoen, Herten (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/810,671

(22) Filed: Mar. 29, 2004

(65) Prior Publication Data
US 2004/0191198 A1 Sep. 30, 2004

(30) Foreign Application Priority Data
Mar. 27, 2003 (DE) ................. 103 13 981
Jul. 1, 2003 (DE) ................. 103 29 780

(51) Int. Cl.
*C09D 17/00* (2006.01)
(52) U.S. Cl. .................. 106/499; 106/415; 106/489; 510/108; 510/119; 510/130; 424/63; 424/401; 424/49; 424/70.7; 424/56; 424/400
(58) Field of Classification Search ................ 106/415, 106/417, 493; 424/63
See application file for complete search history.

(56) References Cited

U.S. PATENT DOCUMENTS

| | | | |
|---|---|---|---|
| 3,929,501 A | 12/1975 | Dunn | |
| 4,200,474 A | 4/1980 | Morris | |
| 5,451,632 A | 9/1995 | Okumura et al. | |
| 5,565,025 A | 10/1996 | Schraml-Marth | |
| 5,753,371 A * | 5/1998 | Sullivan et al. | ............. 428/406 |
| 5,780,018 A | 7/1998 | Collins et al. | |
| 6,045,914 A * | 4/2000 | Sullivan et al. | ............. 428/404 |
| 6,060,071 A * | 5/2000 | Motitschke et al. | ......... 424/401 |
| 6,419,736 B1 | 7/2002 | Pfaff et al. | |
| 6,517,628 B1 * | 2/2003 | Pfaff et al. | .................. 106/417 |
| 6,596,070 B1 | 7/2003 | Schmidt et al. | |
| 6,875,264 B2 * | 4/2005 | Zimmermann et al. | ...... 106/446 |
| 2004/0123778 A1 * | 7/2004 | Bagala | ........................ 106/415 |
| 2005/0220741 A1 * | 10/2005 | Dumousseaux | ............... 424/64 |

FOREIGN PATENT DOCUMENTS

| | | | |
|---|---|---|---|
| DE | WO 02/090448 | * | 11/2002 |
| DE | WO 03/006558 | * | 1/2003 |
| JP | 2001-11340 | * | 1/2001 |
| WO | WO 99/20695 | | 4/1999 |
| WO | WO 99/46336 | | 9/1999 |
| WO | WO 2002/090448 | * | 11/2002 |

OTHER PUBLICATIONS

Englehard Chameleon Galaxy Plum Nail Enamel brochure published 2000.*
Engelhard Styling Gel publication brochure published 2000.*
Engelhard Smokes and Sparkles Body Powder Misty Taupe brochur published 2002.*
IP.com posting published Feb. 6, 2002.*

* cited by examiner

*Primary Examiner*—C. Melissa Koslow
(74) *Attorney, Agent, or Firm*—Millen, White, Zelano & Branigan, P.C.

(57) ABSTRACT

Pigment mixtures which have at least two components, where component A comprises effect pigments based on glass flakes and component B comprises flake-form, needle-shaped, spherical or crystalline colorants or fillers, and to the use thereof, in particular in cosmetic formulations and for the coloring or as a coating of products in the foods and pharmaceuticals sector are described.

14 Claims, No Drawings

PIGMENT MIXTURE, AND THE USE THEREOF IN COSMETICS AND IN THE FOODS AND PHARMACEUTICALS SECTOR

The present invention relates to a pigment mixture consisting of at least two components, where component A comprises effect pigments based on thin glass flakes and component B comprises flake-form, needle-shaped, spherical or crystalline colorants and/or fillers, and to the use thereof in cosmetic formulations and in the foods and pharmaceuticals sector.

Coated and uncoated glass flakes are known, for example from WO 97/46624, WO 03/006558 and WO 02/090448. It is often only with difficulty that hiding power and luster can be achieved simultaneously to a satisfactory extent in flake-form pigments. Thus, mica flakes or $SiO_2$ flakes with one or more thin metal-oxide coating layers, for example, are distinguished by interference colors and high luster, but at the same time, owing to the transparent substrate, also by high transparency and thus comparatively low hiding power.

Effect pigments based on glass flakes are distinguished by high luster, color purity and tinting strength and should therefore be of interest, in particular, for cosmetics.

An object of the present invention is to provide effect pigments based on glass flakes in such a way that they have comparatively high hiding power, can be incorporated well into the respective application system and at the same time do not influence the optical properties, such as, in particular, the luster and color purity, at all, or only do so to an insignificant extent.

Upon further study of the specification and appended claims, further objects and advantages of this invention will become apparent to those skilled in the art.

Surprisingly, a pigment mixture has now been found that has none of the above-mentioned disadvantages. The pigment mixture according to the invention consists of at least two components, where component A comprises effect pigments based on thin glass flakes and component B comprises flake-form, needle-shaped, spherical or crystalline colorants and/or fillers.

The admixture of one or more colorants to the coated glass flakes enables a rainbow effect to be imparted on the application systems, increases the color effect and achieves novel color effects. Furthermore, the pigment mixtures are distinguished by high luster, a sparkle effect and skin feeling.

The invention thus includes pigment mixtures consisting of at least two components, where component A comprises effect pigments based on thin glass flakes and component B comprises flake-form, needle-shaped, spherical or crystalline colorants and/or fillers.

The invention further includes cosmetic formulations, such as, for example, make-ups, compact powders, loose powders, lipsticks, lotions, emulsions, etc., which comprise the pigment mixture according to the invention. The pigment mixtures are furthermore suitable for colorings and colored coatings of foods and pharmaceutical products, such as, for example, medicament coatings of tablets, coated tablets, gelatine capsules, etc.

The coated glass flakes can be mixed with the colorant or filler in any ratio. The ratio of component A to component B is preferably from 95:5 to 5:95, in particular from 80:20 to 20:80, very particularly preferably from 70:30 to 30:70.

The effect pigments are preferably glass flakes coated with one or more metal oxides, particularly of titanium, silicon, iron, chromium or mixtures thereof. Particularly, preferred effect pigments have the following structure:

glass flake+$TiO_2$ layer glass flake+$SiO_2$ layer+$TiO_2$ layer glass flake+$Fe_2O_3$ layer glass flake+$SiO_2$ layer+$Fe_2O_3$ layer glass flake+$Fe_3O_4$ layer glass flake+$SiO_2$ layer+$Fe_3O_4$ layer glass flake+$TiFe_2O_3$ layer glass flake+$SiO_2$ layer+$TiFe_2O_3$ layer glass flake+$Cr_2O_3$ layer glass flake+$SiO_2$ layer+$Cr_2O_3$ layer glass flake+$TiO_2$ layer+$Cr_2O_3$ layer glass flake+$SiO_2$ layer+$TiO_2$ layer+$Cr_2O_3$ layer glass flake+titanium suboxide glass flake+$SiO_2$ layer+titanium suboxide glass flake+$TiO_2$ layer+$Fe_2O_3$ layer glass flake+$SiO_2$ layer+$TiO_2$ layer+$Fe_2O_3$ layer glass flake+$TiO_2$ layer+Berlin Blue glass flake+$SiO_2$ layer+$TiO_2$ layer+Prussian Blue glass flake+$TiO_2$ layer+Carmine Red glass flake+$SiO_2$ layer+$TiO_2$ layer+Carmine Red glass flake+$TiO_2$ layer+DC Red 30 glass flake+$SiO_2$ layer+$TiO_2$ layer+DC Red 30 glass flake+$Fe_2O_3$ layer+$SiO_2$ layer+$Fe_2O_3$ layer glass flake+$Fe_2O_3$ layer+$SiO_2$ layer+$TiO_2$ layer glass flake+$TiO_2$ layer+$SiO_2$ layer+$Fe_2O_3$ layer glass flake+$TiO_2$ layer+$SiO_2$ layer+$TiO_2/Fe_2O_3$ layer glass flake+$TiO_2/Fe_2O_3$ layer+$SiO_2$ layer+$TiO_2/Fe_2O_3$ layer glass flake+$TiO_2$ layer+$SiO_2$ layer+$Cr_2O_3$ layer The $TiO_2$ layer is preferably in the rutile or anatase modification.

Especially preferred are glass flakes coated first with a $SiO_2$ layer and further coated with one or more metal oxides and optionally with Carmine Red, Prussian Blue or an organic dye. The metal oxides are preferably selected from the group of $TiO_2$, Ti suboxides, $Fe_2O_3$, $Fe_3O_4$ and mixtures thereof.

Instead of or in addition to the outer metal-oxide layer, it is also possible to use a semitransparent layer of a metal. Suitable metals for this purpose are, for example, Cr, Ti, Mo, W, Al, Cu, Ag, Au and Ni.

The thickness of the glass flakes is preferably $\leq 1$ μm, in particular $\leq 0.8$ μm and particularly preferably $\leq 0.6$ μm.

Coated glass flakes are commercially available, for example, under the trademark Ronastar from Merck KGaA.

In order to achieve specific color effects, finely divided particles having a size in the nanometer range can additionally be introduced into the high- or low-refractive-index layers, i.e., the metal oxide or metal layers of the effect pigment. Finely divided $TiO_2$ or finely divided carbon (carbon black) having particle sizes in the range 10-250 nm, for example, has proven suitable for this purpose. The light-scattering properties of such particles enable the luster and hiding power to be influenced specifically.

The effect pigments may also be provided with a protective layer in order to improve the light, weather and chemical stability or in order to increase the compatibility in various media. Suitable post-coatings or post-treatments are, for example, silanes, silicones, adsorbent silicones, metal soaps, amino acids, lecithins, fluorine components, polyethylenes, collagen or the processes described in DE 22 15 191, DE 31 51 354, DE 32 35 017 or DE 33 34 598. The substances additionally applied preferably make up only from about 0.1 to 5% by weight, more preferably from 0.5 to 3.0% by weight, of the pigment.

Suitable as component B for the pigment mixture according to the invention are all flake-form, needle-shaped, spherical and crystalline colorants or fillers which are known to the person skilled in the art, in particular those which have a particle size of from 0.001 to 10 μm, preferably from 0.01 to 1 μm. The pigment mixtures according to the invention preferably comprise absorption pigments as colorants and flake-form or spherical powders as fillers. Component B preferably comprises coated or uncoated $SiO_2$ beads. $SiO_2$ beads coated with one or more metal oxides are disclosed, for example, in EP 0 803 550 A2. Also preferred as colorant (component B) are, in particular, pearlescent pigments, including multilayered pigments or interference pigments. The pearlescent pigments used are pigments based on flake-form, transparent or semitransparent substrates comprising, for example, phyllosilicates, such as, for example, natural or synthetic mica, talc, sericite, kaolin or other silicate materials, coated with colored or colorless metal oxides, such as, for example, $TiO_2$, titanium suboxides, titanium oxynitrides, $Fe_2O_3$, $Fe_3O_4$, $SnO_2$, $Cr_2O_3$, ZnO, CuO, NiO and other metal oxides, alone or in a mixture, in a single layer or in successive layers.

Pearlescent pigments are disclosed, for example, in German Patents and Patent Applications 14 67 468, 19 59 998, 20 09 566, 22 14 454, 22 15 191, 22 44 298, 23 13 331, 25 22 572, 31 37 808, 31 37 809, 31 51 343, 31 51 354, 31 51 355, 32 11 602, 32 35 017 and P 38 42 330 and are commercially available, for example under the trademarks Iriodin®, Timiron® and Xirona® from Merck KGaA, Darmstadt, Germany and/or Rona, USA. Particularly preferred pigment compositions comprise $TiO_2$/mica, $Fe_2O_3$/mica and/or $TiO_2$/$Fe_2O_3$/mica pigments.

Preference is furthermore given to coated or uncoated BiOCl pigments, $TiO_2$— and/or $Fe_2O_3$-coated $SiO_2$ or $Al_2O_3$ flakes. The coating of the $SiO_2$ flakes with one or more metal oxides can be carried out, for example, as described in WO 93/08237 (wet-chemical coating) or DE-A 196 14 637 (CVD process).

The multilayered pigments disclosed, for example, in DE-A 196 18 563, DE-A 196 18 566, DE-A 196 18 569, DE-A 197 07 805, DE-A 197 07 806 and DE-A 197 46 067 are based on a flake-form, transparent, colored or colorless matrix consisting of mica (synthetic or natural), $SiO_2$ flakes, glass flakes, $Al_2O_3$ flakes or polymer flakes and generally have a thickness of between 0.3 and 5 μm, in particular between 0.4 and 2.0 μm. The size in the other two dimensions is usually between 1 and 250 μm, preferably between 2 and 100 μm, and in particular between 5 and 40 μm. The multilayered pigments consist of the matrix (substrate) coated with metal oxides (at least 2). The coating of the substrate flakes mica, $SiO_2$ flakes, glass flakes or $Al_2O_3$ flakes with a plurality of layers is carried out in such a way that a layer structure preferably consisting of alternating high- and low-refractive-index layers is formed. The multilayered pigments preferably contain 2, 3, 4, 5, 6 or 7 layers, in particular 3, 4 or 5 layers. Suitable high-refractive-index metal oxides are, for example, titanium dioxide, zirconium oxide, zinc oxide, iron oxides, iron/titanium oxides (iron titanates) and/or chromium oxide, in particular $TiO_2$ and/or $Fe_2O_3$. The low-refractive-index metal oxides used are $SiO_2$ and $Al_2O_3$. However, it is also possible to employ $MgF_2$ or an organic polymer (for example acrylate) for this purpose. The coating of the substrate flakes can be carried out, for example, as described in WO 93/08237 (wet-chemical coating) or DE-A-196 14 637 (CVD process).

The interference pigments are preferably pigments based on mica, glass flakes or $SiO_2$ flakes which are coated with colored or colorless metal oxides, such as, for example, $TiO_2$, titanium suboxides, titanium oxynitrides, $Fe_2O_3$, $Fe_3O_4$, $SnO_2$, $Cr_2O_3$, ZnO, CuO, NiO and other metal oxides, alone or in a mixture, in a single layer or in successive layers.

The mixtures according to the invention also include mixtures of effect pigments based on glass (=component A) with interference pigments based on glass (=component B). But component A and component B must be different.

Suitable flake-form colorants are, in particular, pearlescent pigments, in particular based on mica, $SiO_2$ flakes or $Al_2O_3$ flakes, which are only coated with one metal-oxide layer, metal-effect pigments (Al flakes, bronzes), optically variable pigments (OVPs), liquid-crystal polymer pigments (LCPs) or holographic pigments.

The spherical colorants include, in particular, $TiO_2$, colored $SiO_2$, $CaSO_4$, iron oxides, chromium oxides, carbon black, organic colored pigments, such as, for example, anthraquinone pigments, quinacridone pigments, diketopyrrolopyrrole pigments, phthalocyanine pigments, azo pigments and isoindoline pigments. The needle-shaped pigments are preferably BiOCl, colored glass fibers, α-FeOOH, organic colored pigments, such as, for example, azo pigments, β-phthalocyanine CI Blue 15.3, Cromophtal Yellow 8GN (Ciba-Geigy), Irgalith Blue PD56 (Ciba-Geigy), azomethine copper complex CI Yellow 129 or Irgazine Yellow 5GT (Ciba-Geigy).

The pigment mixture according to the invention is simple and easy to handle. The pigment mixture can be incorporated into the application system by simple stirring-in. Complex grinding and dispersion of pigments is unnecessary.

The pigment mixture according to the invention can be used for the pigmenting of food colorings, for the treatment of foods, for example mass coloring or as a coating, in medicament coatings, for example in coated tablets and tablets, or in cosmetic formulations, such as lipsticks, lip gloss, eyeliner, eye shadow, rouge, sunscreens, pre-sun and after-sun compositions, make-ups, body lotions, bath gels, soaps, bath salts, toothpaste, hair gels, mascara, nail varnishes, compact powders, shampoos, loose powders and gels, etc. The concentration of the pigment mixture in the application system to be pigmented is generally between 0.1 and 70% by weight, preferably between 0.1 and 50% by weight and in particular between 1.0 and 10% by weight, based on the total solids content of the system. It is generally dependent on the specific application and can be up to 100% in the case of loose powders.

The pigment mixture according to the invention can also advantageously be employed in decorative and care cosmetics. The use concentration and the mixing ratio of coated glass flakes with component B, in particular organic and inorganic colored pigments and dyes, of natural or synthetic origin, such as, for example, chromium oxide, ultramarine, spherical $SiO_2$ or $TiO_2$ pigments, are dependent on the application medium and the effect that is to be achieved.

The use concentration extends from 0.01% by weight in shampoo to 70% by weight in compact powders. In a mixture of coated glass flakes with spherical fillers, for example $SiO_2$, the concentration can be 0.01-70% by weight in the formulation. The cosmetic products, such as, for example, nail varnishes, lipsticks, compact powders, shampoos, loose powders and gels, are distinguished by particularly interesting luster effects. The sparkle effect in nail varnish can be significantly increased compared with conventional nail varnishes with the aid of the pigment mixtures according to the invention.

Coated glass flakes can be mixed with other pigments or dyes in all ratios, preferably in a ratio of from 1:10 to 10:1.

The pigment mixture according to the invention can furthermore be mixed with commercially available fillers. Fillers which may be mentioned are, for example, natural and synthetic mica, glass beads or glass powder, nylon powder, pure or filled melamine resins, talc, glasses, kaolin, oxides or hydroxides of aluminum, magnesium, calcium or zinc, BiOCl, barium sulfate, calcium sulfate, calcium carbonate, magnesium carbonate, carbon, and physical or chemical combinations of these substances.

There are no restrictions regarding the particle shape of the filler. In accordance with requirements, it can be, for example, flake-form, spherical, needle-shaped, crystalline or amorphous.

The pigments according to the invention can of course also be combined in the formulations with cosmetic raw materials and auxiliaries of any type. These include, inter alia, oils, fats, waxes, film formers, surfactants, antioxidants, such as, for example, vitamin C or vitamin E, stabilizers, odor intensifiers, silicone oils, emulsifiers, solvents, such as, for example, ethanol, or ethyl acetate or butyl acetate, preservatives and auxiliaries which generally determine applicational properties, such as, for example, thickeners and rheological additives, such as, for example, bentonites, hectorites, silicon dioxides, Ca silicates, gelatines, high-molecular-weight carbohydrates and/or surface-active auxiliaries, etc.

The formulations comprising the pigment mixtures according to the invention can belong to the lipophilic, hydrophilic or hydrophobic type. In the case of heterogeneous formulations having discrete aqueous and non-aqueous phases, the pigment mixtures according to the invention may in each case be present in only one of the two phases or alternatively distributed over both phases.

The pH values of the formulations can be between 1 and 14, preferably between 2 and 11 and particularly preferably between 5 and 8.

No limits are set for the concentrations of the pigment mixtures according to the invention in the formulation. They can be—depending on the application—between 0.001 (rinse-off products, for example shower gels) and 100% (for example effect-effect articles for particular applications).

The pigments according to the invention may furthermore also be combined with cosmetic active ingredients. Suitable active ingredients are, for example, insect repellents, inorganic UV filters, such as, fore example, $TiO_2$, UV A/BC protective filters (for example OMC, B3 and MBC), also in encapsulated form, anti-ageing active ingredients, vitamins and derivatives thereof (for example vitamin A, C, E, etc.), self-tanning agents (for example DHA, erythrulose, inter alia), and further cosmetic active ingredients, such as, for example, bisabolol, LPO, VTA, ectoin, emblica, allantoin, bioflavonoids and derivatives thereof.

Organic UV filters are generally incorporated into cosmetic formulations in an amount of from 0.5 to 10 per cent by weight, preferably 1-8%, and inorganic filters in an amount of from 0.1 to 30%.

The preparations according to the invention may in addition comprise further conventional skin-protecting or skin-care active ingredients. These may in principle be any active ingredients known to the person skilled in the art.

Particularly preferred active ingredients are pyrimidinecarboxylic acids and/or aryl oximes.

Of the cosmetic applications, particular mention should be made of the use of ectoin and ectoin derivatives for the care of aged, dry or irritated skin. Thus, European Patent Application EP-A-0 671 1 describes, in particular, that ectoin and hydroxyectoin are employed in cosmetic preparations, such as powders, soaps, surfactant-containing cleansing products, lipsticks, rouge, make-up, care creams and sunscreen compositions.

Application forms of the cosmetic formulations which may be mentioned are, for example: solutions, suspensions, emulsions, PIT emulsions, pastes, ointments, gels, creams, lotions, powders, soaps, surfactant-containing cleansing preparations, oils, aerosols and sprays. Examples of other application forms are sticks, shampoos and shower preparations. Any desired customary excipients, auxiliaries and, if desired, further active ingredients may be added to the preparation.

Ointments, pastes, creams and gels may comprise the customary excipients, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary excipients, for example lactose, talc, silica, aluminum hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary excipients, such as solvents, solubilizers and emulsifiers, for example water, ethanol, isopropanol, ethyl carbonate, ethyl acetate, benzyl alcohol, benzyl benzoate, propylene glycol, 1.3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

Suspensions may comprise the customary excipients, such as liquid diluents, for example water, ethanol or propylene glycol, suspending agents, for example ethoxylated isostearyl alcohols, polyoxyethylene sorbitol esters and polyoxyethylene sorbitan esters, microcrystalline cellulose, aluminum metahydroxide, bentonite, agar-agar and tragacanth, or mixtures of these substances.

Soaps may comprise the customary excipients, such as alkali metal salts of fatty acids, salts of fatty acid monoesters, fatty acid protein hydrolysates, isethionates, lanolin, fatty alcohol, vegetable oils, plant extracts, glycerol, sugars, or mixtures of these substances.

Surfactant-containing cleansing products may comprise the customary excipients, such as salts of fatty alcohol sulfates, fatty alcohol ether sulfates, sulfosuccinic acid monoesters, fatty acid protein hydrolysates, isethionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary excipients, such as synthetic oils, such as, for example, fatty acid esters, fatty alcohols, silicone oils, natural oils, such as vegetable oils and oily plant extracts, paraffin oils, lanolin oils, or mixtures of these substances.

The cosmetic preparations may exist in various forms. Thus, they can be, for example, a solution, a water-free preparation, an emulsion or microemulsion of the water-in-oil (W/O) or oil-in-water (O/W) type, a multiple emulsion, for example of the water-in-oil-in-water (W/O/W) type, a gel, a solid stick, an ointment or an aerosol. It is also advantageous to administer ectoins in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favorable. Preference is given to emulsions. O/W emulsions are particularly preferred. Emulsions, W/O emulsions and O/W emulsions are obtainable in a conventional manner.

Further embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

Solid sticks consist of natural or synthetic waxes and oils, fatty alcohols, fatty acids, fatty acid esters, lanolin and other fatty substances.

If a preparation is formulated as an aerosol, the customary propellants, such as alkanes, fluoroalkanes and chlorofluoroalkanes, are generally used.

The cosmetic preparation may also be used to protect the hair against photochemical damage in order to prevent color changes, bleaching or damage of a mechanical nature. In this case, a suitable formulation is in the form of a rinse-out shampoo, lotion, gel or emulsion, the preparation in question being applied before or after shampooing, before or after coloring or bleaching or before or after permanent waving. It is also possible to select a preparation in the form of a lotion or gel for styling or treating the hair, in the form of a lotion or gel for brushing or blow-waving, in the form of a hair lacquer, permanent waving composition, colorant or bleach for the hair. The preparation having light-protection properties may comprise adjuvants, such as surfactants, thickeners, polymers, softeners, preservatives, foam stabilizers, electrolytes, organic solvents, silicone derivatives, oils, waxes, antigrease agents, dyes and/or pigments which color the composition itself or the hair, or other ingredients usually used for hair care.

The pharmaceutical and food products are colored by adding the pigment mixture, preferably consisting of pigment and colorants, such as, for example, natural or nature-identical dyes, in the desired mixing ratios to the product to be colored in amounts of from 0.005 to 15% by weight, preferably from 0.01 to 10% by weight.

Products suitable for coloring that may be mentioned are, in particular, coatings on all types of foods, in particular pigmented sugar and shellac coatings (alcoholic and aqueous), coatings with oils and waxes, with gum arabic and with cellulose grades (for example HPMC=hydroxypropylmethylcellulose), the incorporation into or application to sugar products, cake decorations, compresses, coated tablets, chewing gum, gum products, fondant products, marzipan products, filling compositions, cocoa and fat glazes, chocolate and chocolate-containing products, ice cream, cereals, snack products, coating compositions, cake glazes, scattered sugar decorations, nonpareils, jelly and gelatine products, sweets, liquorice, icing, candyfloss, fat, sugar and cream compositions, blancmange, desserts, flan glaze, cold fruit soups, sodas and carbonated drinks, beverages with stabilizing additives, such as, for example, carboxymethylcellulose, acidified and unacidified milk products, such as, for example, quark, yoghurt, cheese, cheese rinds, sausage casings, etc.

A further major area of application is in the pharmaceuticals and OTC sector for coloring or coating tablets, gelatine capsules, coated tablets, ointments, cough mixture, etc. In combination with conventional coatings, such as polymethacrylates and cellulose grades, such as HPMC, the pigment mixtures can be employed in a variety of ways for coloring.

The invention thus also relates to formulations comprising the pigment mixture according to the invention.

The entire disclosures of all applications, patents and publications, cited herein and of corresponding German application No. 10329780.4, filed Jul. 1, 2003, and German Application No. 10313981.8, filed Mar. 27, 2003, is incorporated by reference herein.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

Example 1
Shimmering Foundation

| Raw material | Source of supply | INCI | [%] |
|---|---|---|---|
| Phase A | | | |
| Extender W <15 μm | Merck KGaA/Rona ® | Mica, CI 77891 (Titanium Dioxide) | 9.00 |
| MICRONA ® Matte Yellow <15 μm | Merck KGaA/Rona ® | Mica, CI 77492 (Iron Oxides) | 4.00 |
| MICRONA ® Matte Red <15 μm | Merck KGaA/Rona ® | CI 77491 (Iron Oxides), Mica | 0.40 |
| MICRONA ® Matte Black <15 μm | Merck KGaA/Rona ® | CI 77499 (Iron Oxides), Mica | 0.30 |
| Glass flakes with $TiO_2$ (interference gold) 10-80 μm | Merck KGaA/Rona ® | Glass, Silica, CI 77891 (Titanium Dioxide), Tin Oxide | 4.50 |
| RONASPHERE ® <10 μm | Merck KGaA/Rona ® | Silica | 5.00 |
| Phase B | | | |
| Blanose 7 HF | Aqualon GmbH | Cellulose Gum | 0.20 |
| Veegum | Vanderbilt | Magnesium Aluminum Silicate | 1.00 |
| Texapon K 1296 | Cognis GmbH | Sodium Lauryl Sulfate | 0.60 |
| Triethanolamine extra pure | Merck KGaA/Rona ® | Triethanolamine | 0.50 |
| Titriplex III | Merck KGaA/Rona ® | Disodium EDTA | 0.25 |
| Methyl 4-hydroxybenzoate | Merck KGaA/Rona ® | Methylparaben | 0.15 |
| 1.2-Propanediol | Merck KGaA/Rona ® | Propylene Glycol | 10.90 |
| Water, demineralized | | Aqua (Water) | 42.95 |
| Phase C | | | |
| Isopropyl myristate | Cognis GmbH | Isopropyl Myristate | 8.00 |
| Liquid paraffin | Merck KGaA/Rona ® | Paraffinum Liquidum (Mineral Oil) | 3.60 |
| Crodamol SS | Croda GmbH | Cetyl Esters | 2.60 |
| Monomuls 60-35 C | Cognis GmbH | Hydrogenated Palm Glycerides | 1.70 |
| Stearic acid | Merck KGaA/Rona ® | Stearic Acid | 1.50 |
| EUSOLEX ® 6300 | Merck KGaA/Rona ® | 4-Methylbenzylidene Camphor | 1.30 |
| EUSOLEX ® 4360 | Merck KGaA/Rona ® | Benzophenone-3 | 0.50 |
| Rona Care ™ tocopherol acetate | Merck KGaA/Rona ® | Tocopheryl Acetate | 0.50 |
| Magnesium stearate | Merck KGaA/Rona ® | Magnesium Stearate | 0.10 |
| Propyl 4-hydroxybenzoate | Merck KGaA/Rona ® | Propylparaben | 0.05 |
| Phase D | | | |
| Perfume oil 200529 | Fragrance Resources | Parfum | 0.20 |
| Euxyl K 400 | Schülke & Mayr GmbH | Phenoxethanol, Methyldibromo Glutaronitrile | 0.20 |

Preparation:

Melt all constituents of phase C at about 75° C. and stir until everything has melted. Initially introduce the water of phase B cold, homogenize in the Blanose using the Turrax, scatter in the Veegum and re-homogenize. Warm to 75° C. and dissolve the other constituents therein with stirring. Stir in the constituents of phase A. Add phase C at 75° C. with stirring and homogenize for 2 minutes. Cool the mass to 40° C. with stirring, add phase D. Cool further to room temperature with stirring and adjust to pH 6.0-6.5 (for example using citric acid solution).

Example 2

Shower Gel

| Raw material | Source of supply | INCI | [%] |
|---|---|---|---|
| Phase A | | | |
| Glass flakes with $TiO_2$ and $Fe_2O_3$ (gold pigment) 20-200 μm | Merck KGaA/Rona ® | Glass, Silica, CI 77891 (Titanium Dioxide), CI 77491 (Iron Oxides) | 0.10 |

-continued

| Raw material | Source of supply | INCI | [%] |
|---|---|---|---|
| Keltrol T | Kelco | Xanthan Gum | 0.75 |
| Water, demineralized | | Aqua (Water) | 64.95 |
| Phase B | | | |
| Plantacare 2000 UP | Cognis GmbH | Decyl Glucoside | 20.00 |
| Texapon ASV 50 | Cognis GmbH | Sodium Laureth Sulfate, Sodium Laureth-8 Sulfate, Magnesium Laureth Sulfate, Magnesium Laureth-8 Sulfate, Sodium Oleth Sulfate, Magnesium Oleth Sulfate | 3.60 |
| Bronidox L | Cognis GmbH | Propylene Glycol, 5-Bromo-5-Nitro-1,3-Dioxane | 0.20 |
| Perfume oil Everest 79658 SB | Haarmann & Reimer GmbH | Parfum | 0.05 |
| 1% FD&C Blue No. 1 in water | BASF AG | Aqua (Water), CI 42090 (FD&C Blue No. 1) | 0.20 |
| Phase C | | | |
| Citric acid monohydrate | Merck KGaA/Rona ® | Citric Acid | 0.15 |
| Water, demineralized | | Aqua (Water) | 10.00 |

Preparation:

For phase A, stir the pigment into the water. Scatter in the Keltrol T slowly with stirring and stir until it has dissolved. Add phases B and C successively while stirring slowly until everything is homogeneously distributed. Adjust the pH to from 6.0 to 6.4.

Example 3

Eyeliner Gel

| Raw material | Source of supply | INCI | [%] |
|---|---|---|---|
| Phase A | | | |
| Glass flakes with TiO$_2$ (silver pigment) 20-200 µm | Merck KGaA/Rona ® | Glass, Silica, CI 77891 (Titanium Dioxide), Tin Oxide | 5.00 |
| Xirona ® Magic Mauve 5-50 µm | Merck KGaA/Rona ® | Silica, CI 77891 (Titanium Dioxide), Tin Oxide | 10.00 |
| Mica Black 10-60 µm | Merck KGaA/Rona ® | CI 77499 (Iron Oxides), MICA, CI 77891 (Titanium Dioxide) | 5.00 |
| RONASPHERE ® <10 µm | Merck KGaA/Rona ® | Silica | 2.00 |
| Carbopol ETD 2001 | BF Goodrich | Carbomer | 0.40 |
| Citric acid monohydrate | Merck KGaA/Rona ® | Citric Acid | 0.00 |
| Water, demineralized | | Aqua (Water) | 60.00 |
| Phase B | | | |
| Glycerol, anhydrous | Merck KGaA/Rona ® | Glycerin | 4.00 |
| Triethanolamine extra pure | Merck KGaA/Rona ® | Triethanolamine | 0.90 |
| Luviskol VA 64 powder | BASF AG | PVP/VA Copolymer | 2.00 |
| Germaben II | ISP Global Technologies | Propylene Glycol, Diazolidinyl Urea, Methylparaben, Propylparaben | 1.00 |
| Water, demineralized | | Aqua (Water) | 9.70 |

Preparation:

Disperse the pearlescent pigments and Ronasphere® in the water of phase A. Acidify using a few drops of citric acid in order to reduce the viscosity and scatter in the Carbopol with stirring. When completely dissolved, slowly stir in the pre-dissolved phase B, and adjust the pH to from 7.0 to 7.5.

Example 4

Eye Shadow

| Raw material | Source of supply | INCI | [%] |
|---|---|---|---|
| Phase A | | | |
| Xirona ® Caribbean Blue 10-60 μm | Merck KGaA/Rona ® | Silica, CI 77891 (Titanium Dioxide), Mica, Tin Oxide | 45.00 |
| Glass flakes with TiO$_2$ (silver pigment) 20-200 μm | Merck KGaA/Rona ® | Glass, Silica, CI 77891 (Titanium Dioxide), Tin Oxide | 10.00 |
| BIRON ® B 50 2-35 μm | Merck KGaA/Rona ® | CI 77163 (Bismuth Oxychloride) | 3.00 |
| Colorona ® Dark Blue 10-60 μm | Merck KGaA/Rona ® | MICA, CI 77891 (Titanium Dioxide), CI 77510 (Ferric Ferrocyanide) | 10.00 |
| Magnesium stearate | Merck KGaA/Rona ® | Magnesium Stearate | 2.50 |
| White clay | Merck KGaA/Rona ® | Kaolin | 5.00 |
| Hubersorb 600 | J. M. Huber Corp. | Calcium Stearate | 0.50 |
| Talc | Merck KGaA/Rona ® | Talc | 11.00 |
| Phase B | | | |
| Amerchol L 101 | Amerchol | Lanolin Alcohol, Paraffinum Liquidum (Mineral Oil) | 10.70 |
| Super Hartolan | Croda GmbH | Lanolin Alcohol | 1.00 |
| Ewalin 1751 | H. Erhard Wagner GmbH | Petrolatum | 1.00 |
| Propyl 4-hydroxybenzoate | Merck KGaA/Rona ® | Propylparaben | 0.10 |
| Perfume oil Elegance # 79228 D MF | Haarmann & Reimer GmbH | Parfum | 0.20 |

Preparation:

Combine and pre-mix the constituents of phase A. Subsequently add the molten phase B dropwise to the powder mixture with stirring. The powders are pressed at from 40 to 50 bar.

Example 5

Eye Shadow Gel

| Raw material | Source of supply | INCI | [%] |
|---|---|---|---|
| Phase A | | | |
| Xirona ® Indian Summer 5-50 μm | Merck KGaA/Rona ® | Silica, CI 77491 (Iron Oxides) | 15.00 |
| Glass flakes with Fe$_2$O$_3$ 10-80 μm | Merck KGaA/Rona ® | Glass, Silica, CI 77491 (Iron Oxides) | 5.00 |
| RONASPHERE ® <10 μm | Merck KGaA/Rona ® | Silica | 3.00 |
| Carbopol ETD 2001 | BF Goodrich GmbH | Carbomer | 0.30 |
| Citric acid monohydrate | Merck KGaA/Rona ® | Citric Acid | 0.00 |
| Water, demineralized | | Aqua (Water) | 60.00 |

-continued

| Raw material | Source of supply | INCI | [%] |
|---|---|---|---|
| Phase B | | | |
| Glycerol, anhydrous | Merck KGaA/Rona ® | Glycerin | 2.00 |
| Germaben II | ISP Global Technologies | Propylene Glycol, Diazolidinyl Urea, Methyl paraben, Propylparaben | 0.20 |
| Triethanolamine extra pure | Merck KGaA/Rona ® | Triethanolamine | 0.70 |
| Water, demineralized | | Aqua (Water) | 13.80 |

Preparation:

Disperse the pearlescent pigments and Ronasphere® in the water of phase A. Acidify using a few drops of citric acid in order to reduce the viscosity, and scatter in the Carbopol with stirring. When completely dissolved, slowly stir in the pre-dissolved phase B.

Example 6
Eye Shadow

| Raw material | Source of supply | INCI | [%] |
|---|---|---|---|
| Phase A | | | |
| Xirona ® Caribbean Blue 10-60 μm | Merck KGaA/Rona ® | Silica, CI 77891 (Titanium Dioxide), MICA, TIN Oxide | 20.00 |
| Colorona ® Dark Blue 10-60 μm | Merck KGaA/Rona ® | MICA, CI 77891 (Titanium Dioxide), CI 77510 (Ferric Ferrocyanide) | 5.00 |
| Glass flakes with $TiO_2$ (silver pigment) 20-200 μm | Merck KGaA/Rona ® | Glass, Silica, CI 77891 (Titanium Dioxide), Tin Oxide | 5.00 |
| Talc | Merck KGaA/Rona ® | Talc | 49.50 |
| Potato starch | Sudstarke GmbH | Solanum Tuberosum (Potato Starch) | 7.50 |
| Magnesium stearate | Merck KGaA/Rona ® | Magnesium Stearate | 2.50 |
| Phase B: | | | |
| Isopropyl stearate | Cognis GmbH | Isopropyl Stearate | 9.14 |
| Cetyl palmitate | Merck KGaA/Rona ® | Cetyl Palmitate | 0.53 |
| Ewalin 1751 | H. Erhard Wagner GmbH | Petrolatum | 0.53 |
| Perfume oil Elegance # 79228 D MF | Haarmann & Reimer GmbH | Parfum | 0.20 |
| Propyl 4-hydroxybenzoate | Merck KGaA/Rona ® | Propylparaben | 0.10 |

Preparation:

Combine and pre-mix the constituents of phase A. Subsequently add the molten phase B dropwise to the powder mixture with stirring. The powders are pressed at from 40 to 50 bar.

Example 7
Nail Varnish

| Raw material | Source of supply | INCI | [%] |
|---|---|---|---|
| Glass flakes with $TiO_2$ (silver pigment) 20-200 μm | Merck KGaA/Rona ® | Glass, Silica, CI 77891 (Titanium Dioxide), Tin Oxide | 1.50 |

| Raw material | Source of supply | INCI | [%] |
| --- | --- | --- | --- |
| Colorona ® Oriental Beige 10-60 μm | Merck KGaA/Rona ® | Mica, CI 77891 (Titanium Dioxide), CI 77491 (Iron Oxides) | 0.30 |
| Thixotropic nail varnish base 1348 | International Lacquers S.A. | Toluene, Ethyl Acetate, Butyl Acetate, Nitrocellulose, Tosylamide/Form-aldehyde Resin, Dibutyl Phthalate, Isopropyl Alcohol, Stearalkonium Hectorite, Camphor, Acrylates Copolymer, Benzophenone-1 | 97.90 |
| Red HO 59 | International Lacquers S.A. | Ethyl Acetate, Butyl Acetate, Nitrocellulose, Phthalic Anhydride/Trimellitic Anhydride/Glycols Copolymer, CI 15850 (D&C Red No. 6), Acetyl Tributyl Citrate, Isopropyl Alcohol, Acrylates Crosspolymer | 0.30 |

Preparation:

The pigment is weighed out together with the varnish base and the color dispersion, mixed well by hand using a spatula and subsequently stirred at 1000 rpm for 10 minutes.

Example 8

Lip Lacquer

| Raw material | Source of supply | INCI | [%] |
| --- | --- | --- | --- |
| Phase A | | | |
| Glass flakes with TiO$_2$ (silver pigment) 20-200 μm | Merck KGaA/Rona ® | Glass, Silica, CI 77891 (Titanium Dioxide), Tin Oxide | 2.50 |
| Timiron ® Splendid Violet 10-60 μm | Merck KGaA/Rona ® | CI 77891 (Titanium Dioxide), Mica, Silica | 5.00 |
| Xirona ® Indian Summer 5-50 μm | Merck KGaA/Rona ® | Silica, CI 77491 (Iron Oxides) | 2.50 |
| Rubis Covapate W 4765 | Les Colorants Wackherr | Ricinus Communis (Castor Oil), CI 15850 (D&C Red No. 7 Calcium Lake) | 5.00 |
| Phase B: | | | |
| Foralyn 5020-Ft | Hercules BV | Methyl Hydrogenated Rosinate | 20.00 |
| Adeps Lanae | Henry Lamotte GmbH | Lanolin | 18.00 |
| Castor oil | Henry Lamotte GmbH | Ricinus Communis (Castor Oil) | 13.75 |
| Foral 85-E | Hercules BV | Glyceryl Hydrogenated Rosinate | 12.00 |
| Jojoba oil | Gustav Heess GmbH | Buxus chinensis (Jojoba Oil) | 5.00 |

-continued

| Raw material | Source of supply | INCI | [%] |
|---|---|---|---|
| EUSOLEX ® 2292 | Merck KGaA/Rona ® | Ethylhexyl Methoxycinnamate, BHT | 3.00 |
| Antaron V-216 | ISP Global Technologies | PVP/Hexadecene Copolymer | 4.00 |
| Candelilla wax 2039 L | Kahl & Co. | Candelilla Cera (Cendalilla Wax) | 3.50 |
| Amerchol L 101 | Amerchol | Lanolin alcohol, Paraffinum Liquidum (Mineral Oil) | 3.00 |
| Rohagit S | Rohm GmbH | Acrylates Copolymer | 1.50 |
| Beeswax white | Merck KGaA/Rona ® | Cera Alba (Beeswax) | 1.00 |
| Propyl 4-hydroxybenzoate | Merck KGaA/Rona ® | Propylparaben | 0.10 |
| OXYNEX ® K liquid | Merck KGaA/Rona ® | PEG-8, Tocopherol, Ascorbyl Palmitate, Ascorbic Acid, Citric Acid | 0.05 |
| Phase C | | | |
| Fragrance Tendresse # 75418C | Haarmann & Reimer GmbH | Parfum | 0.10 |

Preparation:

Heat all constituents of phase B to 80° C. (apart from the Foral 85-E). Add the Foral 85-E with stirring. Subsequently add phase A and phase C to the molten phase B. The homogeneous melt is poured into casting moulds pre-warmed to 50° C.

Example 9

Shampoo

| Raw material | Source of supply | INCI | [%] |
|---|---|---|---|
| Phase A | | | |
| Glass flakes with Fe₂O₃ 20-200 µm | Merck KGaA/Rona ® | Glass, Silica, CI 77491 (Iron Oxides) | 0.05 |
| Timiron ® Splendid Gold 10-60 µm | Merck KGa/Rona ® | CI 77891 (Titanium Dioxide), Mica, Silica | 0.10 |
| Carbopol ETD 2020 | BF Goodrich GmbH | Acrylates/C10-30 Alkyl Acrylate Crosspolymer | 0.90 |
| Water, demineralized | | Aqua (Water) | 59.80 |
| Phase B: | | | |
| Triethanolamine extra pure | Merck KGaA/Rona ® | Triethanolamine | 0.90 |
| Water, demineralized | | Aqua (Water) | 10.00 |
| Phase C: | | | |
| Plantacare 2000 UP | Cognis GmbH | Decyl Glucoside | 20.00 |
| Texapon ASV | Cognis GmbH | Magnesium Oleth Sulfate, Sodium Oleth Sulfate, Magnesium Laureth-8 Sulfate, Sodium Laureth-8 Sulfate, Magnesium Laureth Sulfate, Sodium Laureth Sulfate | 8.00 |

| Raw material | Source of supply | INCI | [%] |
|---|---|---|---|
| Bronidox L | Cognis GmbH | Propylene Glycol, 5-Bromo-5-Nitro-1,3-Dioxane | 0.20 |
| Perfume oil Everest 79658 SB | Haarmann & Reimer GmbH | Parfum | 0.05 |

Preparation:

For phase A, stir the pigment into the water. Acidify using a few drops of citric acid (10%) in order to reduce the viscosity, and slowly scatter in the Carbopol with stirring. When completely dissolved, slowly add phase B. The constituents of Phase C are then added successively.

Example 10
Shimmering Body Powder

| Raw material | Source of supply | INCI | [%] |
|---|---|---|---|
| Phase A | | | |
| Glass flakes with TiO$_2$ and Fe$_2$O$_3$ (gold pigment) 20-200 μm | Merck KGaA/Rona ® | Glass, Silica, CI 77891 (Titanium Dioxide), CI 77491 (Iron Oxides) | 10.00 |
| Phase B: | | | |
| Talc | Merck KGaA/Rona ® | Talc | 25.00 |
| Bole white powder | Merck KGaA/Rona ® | Kaolin | 29.70 |
| Mica M <15 μm | Merck KGaA/Rona ® | MICA | 15.00 |
| Silk mica <50 μm | Merck KGaA/Rona ® | MICA | 9.50 |
| RONASPHERE ® <10 μm | Merck KGaA/Rona ® | Silica, CI 77891 (Titanium Dioxide), CI 77491 (Iron Oxides) | 4.00 |
| MICRONA ® Matte Yellow <15 μm | Merck KGaA/Rona ® | MICA, CI 77492 (Iron Oxides) | 1.00 |
| MICRONA ® Matte Red <15 μm | Merck KGaA/Rona ® | MICA, CI 77491 (Iron Oxides) | 1.00 |
| Propyl 4-hydroxybenzoate | Merck KGaA/Rona ® | Propylparaben | 0.30 |
| Phase C | | | |
| Cetiol SQ | Cognis GmbH | Squalane | 2.00 |
| Miglyol 812 N | Sasol Germany GmbH | Caprylic/Capric Triglyceride | 2.00 |
| RonaCare ® Tocopherol Acetate | Merck KGaA/Rona ® | Tocopheryl Acetate | 0.20 |
| Elegance | Haarmann & Reimer GmbH | Parfum | 0.30 |

Preparation:

Weigh out all constituents of phase B together and mix homogeneously in a mixer. Subsequently add phase C and mix further, then add phase A and grind briefly until the pearlescent pigment is uniformly distributed.

Example 11
Sparkling Body Cream (O/W)

| Raw material | Source of supply | INCI | [%] |
|---|---|---|---|
| Phase A | | | |
| Glass flakes with TiO$_2$ and Fe$_2$O$_3$ (gold pigment) 10-80 μm | Merck KGaA/Rona ® | Glass, Silica, CI 77891 (Titanium Dioxide), CI 77491 (Iron Oxides) | 1.00 |

-continued

| Raw material | Source of supply | INCI | [%] |
|---|---|---|---|
| Timiron ® Splendid Gold 10-60 μm | Merck KGaA/Rona ® | CI 77891 (Titanium Dioxide), Mica, Silica | 3.00 |
| Carbopol ETD 2001 | BF Goodrich GmbH | Carbomer | 0.60 |
| Citric acid monohydrate | Merck KGaA/Rona ® | Citric Acid | |
| Water, demineralized | | Aqua (Water) | 39.00 |
| | Phase B | | |
| RonaCare ™ Allantoin | Merck KGaA/Rona ® | Allantoin | 0.20 |
| 1.2-Propanediol | Merck KGaA/Rona ® | Propylene Glycol | 3.00 |
| Euxyl K 400 | Schülke & Mayr GmbH | Phenoxethanol, Methyldibromo Glutaronitrile | 0.10 |
| Chemag 2000 | Chemag AG | Imidazolidinyl Urea | 0.30 |
| Methyl 4-hydroxybenzoate | Merck KGaA/Rona ® | Methylparaben | 0.15 |
| Water, demineralized | | Aqua (Water) | 27.65 |
| | Phase C | | |
| Hostaphat KL 340 N | Clariant GmbH | Dilaureth-4-Phosphate | 3.00 |
| Cetyl alcohol | Merck KGaA/Rona ® | Cetyl Alcohol | 2.00 |
| Liquid paraffin | Merck KGaA/Rona ® | Paraffinum Liquidum (Mineral Oil) | 10.00 |
| Cetiol V | Cognis GmbH | Decyl Oleate | 6.00 |
| Propyl 4-hydroxybenzoate | Merck KGaA/Rona ® | Propylparaben | 0.05 |
| | Phase D | | |
| Triethanolamine | Merck KGaA/Rona ® | Triethanolamine | 0.35 |
| Water, demineralized | | Aqua (Water) | 3.50 |
| | Phase E: | | |
| Perfume oil 72979 | Haarmann & Reimer GmbH | Parfum | 0.10 |

Preparation:

Disperse the pearlescent pigment in the water of phase A. If necessary, acidify using a few drops of citric acid in order to reduce the viscosity. Scatter in the Carbopol with stirring. When completely dissolved, slowly stir in the pre-dissolved phase B. Heat phase A/B and phase C to 80° C., stir phase C into phase A/B, homogenize with phase D, neutralize and cool with stirring. Add perfume oil at 40° C. and cool to room temperature with stirring.

Example 12

Lip Gloss

| Raw material | Source of supply | INCI | [%] |
|---|---|---|---|
| | Phase A | | |
| Glass flakes with TiO$_2$ (interference gold) | Merck KGaA/Rona ® | Glass, Silica, CI 77891 (Titanium Dioxide), Tin Oxide | 6.00 |
| Glass flakes with TiO$_2$ (interference blue) | Merck KGaA/Rona ® | Glass, CI 77891 (Titanium Dioxide), Silica, Tin Oxide | 3.00 |
| | Phase B | | |
| Indopol H 100 | BP Amoco | Polybutene | 59.95 |
| Bentone Gel MIO V | Elementis Specialites | Quaternium-18 Hectorite, Propylene Carbonate, Paraffinum Liquidum (Mineral Oil | 20.00 |
| Eutanol G | Cognis GmbH | Octyldodecanol | 6.00 |
| RonaCare ™ tocopherol acetate | Merck KGaA/Rona ® | Tocopheryl Acetate | 1.00 |
| Dow Corning 1403 Fluid | Dow Corning | Dimethiconol, Dimethicone | 3.00 |

-continued

| Raw material | Source of supply | INCI | [%] |
|---|---|---|---|
| Rubis Covapate W 4765 | Les Colorants Wackherr | Ricinus Communis (Castor Oil), CI 15850 (D&C RED NO. 7 Calcium Lake | 1.00 |
| Propyl 4-hydroxybenzoate | | Propylparaben | 0.05 |

Preparation:

All constituents of phase B are weighed out together, heated to 70° C. and stirred well until a homogeneous mass has formed. The pigments are then added, and the mixture is stirred again. The homogeneous mixture is packaged at 50-60° C.

Example 12

Pearlescent Soap

| Raw material | Source of supply | INCI | [%] |
|---|---|---|---|
| Phase A | | | |
| Glass flakes with TiO$_2$ (interference green) 20-200 μm | Merck KGaA/ Rona ® | Glass, Silica, CI 77891 (Titanium Dioxide), Tin Oxide | 0.50 |
| Phase B: | | | |
| Transparent soap base (vegetable) | Dreiring-Seifen seit 1771 | SODIUM PALMATE, AQUA, SODIUM COCOATE, GLYCERIN, PROPYLENE GLYCOL, SORBITOL, SODIUM CHLORIDE, SODIUM HYDROXIDE, TETRASODIUM EDTA, TETRASODIUM ETIDRONATE | 95.00 |
| Water, demineralized | | AQUA (WATER) | 3.50 |
| Perfume oil Soft Touch 50-40 | Cognis GmbH | PARFUM | 1.00 |

Preparation:

All constituents of phase B are mixed three times using a soap extruder through a 0.2 mm sieve and then converted into pellets without a sieve. Phase A is subsequently added and mixed briefly with phase B. The soap composition is re-extruded in the soap line, extruded through a breaker plate (about 2.5 mm) and cut to length.

Example 13

Pearlescent Soap

| Raw material | Source of supply | INCI | [%] |
|---|---|---|---|
| Phase A | | | |
| Glass flakes with TiO$_2$ (silver pigment) 20-200 μm | Merck KGaA/Rona ® | Glass, Silica, CI 77891 (Titanium Dioxide), Tin Oxide | 0.50 |
| Perfume TS 5925B | Quest International | PARFUM | 1.00 |
| Phase B: | | | |
| Prisavon 1984 | Uniqema | SODIUM PALMATE, SODIUM PALM KERNELATE, AQUA (WATER), GLYCERIN, SORBITOL, PALM ACID, PALM KERNEL ACID, TETRASODIUM EDTA, TETRASODIUM ETIDRONATE | 98.50 |

Preparation:

The soap base is weighed and transferred into an amalgamator. The perfume and pearlescent pigment are weighed out together in the same container. They are pre-dispersed together in order to avoid dust formation and in order to obtain a uniform coating of the soap noodles in the premix. The mixing time is about 5 minutes. The constituents are then transferred into the feed shaft of the grinding machine and subjected to the finishing step three times. The soap composition, which is now homogeneous, is subsequently converted into the shape of a bar of soap. During this process, the temperature of the soap composition should be brought to 45° C. in order to obtain a maximum pearlescent effect.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A composition comprising:
a component A which comprises one or more effect pigments based on glass flakes having one of the following layer structures:
glass flake+$TiO_2$ layer;
glass flake+$SiO_2$ layer+$TiO_2$ layer;
glass flake+$Fe_2O_3$ layer;
glass flake+$SiO_2$ layer+$Fe_2O_3$ layer;
glass flake+$Fe_3O_4$ layer;
glass flake+$SiO_2$ layer+$Fe_3O_4$ layer;
glass flake+$TiFe_2O_3$ layer;
glass flake+$SiO_2$ layer+$TiFe_2O_3$ layer;
glass flake+$Cr_2O_3$ layer;
glass flake+$SiO_2$ layer+$Cr_2O_3$ layer;
glass flake+$TiO_2$ layer+$Cr_2O_3$ layer;
glass flake+$SiO_2$ layer+$TiO_2$ layer+$Cr_2O_3$ layer;
glass flake+titanium suboxide;
glass flake+$SiO_2$ layer+titanium suboxide;
glass flake+$TiO_2$ layer+$Fe_2O_3$ layer;
glass flake+$SiO_2$ layer+$TiO_2$ layer+$Fe_2O_3$ layer;
glass flake+$TiO_2$ layer+Berlin Blue;
glass flake+$SiO_2$ layer+$TiO_2$ layer+Prussian Blue;
glass flake+$TiO_2$ layer+Carmine Red;
glass flake+$SiO_2$ layer+$TiO_2$ layer+Carmine Red;
glass flake+$TiO_2$ layer+DC Red 30; or
glass flake+$SiO_2$ layer+$TiO_2$ layer+DC Red 30;
wherein the glass flake has a layer thickness of $\leq 1$ μm, and the $TiO_2$ layers are in the anatase or rutile modification;
and a component B which comprises one or more organic and inorganic flake-form, needle-shaped, spherical or crystalline colorants and/or fillers, provided that at least one colorant or filler of component B is different from at least one effect pigment of component A;
and a cosmetic active ingredient.

2. A composition according to claim 1, wherein component B contains at least one colorant selected from the group consisting of pearlescent pigments, multilayered pigments and interference pigments.

3. A composition according to claim 1, wherein the effect pigment of component A is based on a glass flake having a layer thickness of $\leq 0.6$ μm.

4. A composition according to claim 2, wherein the effect pigment of component A is based on a glass flake having a layer thickness of $\leq 0.6$ μm.

5. A composition according to claim 1, wherein the composition additionally comprises at least one additive which is conventional in cosmetics in addition to the cosmetic active ingredient.

6. A composition according to claim 2, wherein the composition additionally comprises at least one additive which is conventional in cosmetics in addition to the cosmetic active ingredient.

7. A composition according to claim 1, wherein component A and component B are mixed in a weight ratio of from 95:5 to 5:95.

8. A composition according to claim 1, wherein the cosmetic active ingredient is an insect repellant, an inorganic UV filter, an anti-ageing active ingredient, a vitamin, a self-tanning agent, bisabolol, LPO, VTA, ectoin, hydroxyectoin, emblica, allantoin or a bioflavonoid.

9. A composition according to claim 1, wherein the cosmetic active ingredient is ectoin or hydroxyectoin.

10. A composition according to claim 1, wherein component B is a spherical colorant selected from: $TiO_2$, colored $SiO_2$, $CaSO_4$, an iron oxide, a chromium oxides, carbon black, or an organic colored pigment, selected from anthraquinone pigments, quinacridone pigments, diketopyrrolopyrrole pigments, phthalocyanine pigments, azo pigments and isoindoline pigments.

11. A composition according to claim 1, which is in the form of a lipstick, lip gloss, eyeliner, eye shadow, rouge, sunscreen, pre-sun or after-sun skin cosmetic, make-up, body lotion, bath gel, soap, bath salt, toothpaste, hair gel, mascara, nail varnish, compact powder, shampoo, loose powder cosmetic, cosmetic gel, surfactant-containing cleanser, or skin care cream.

12. A composition according to claim 1, wherein the composition further comprises at least one cosmetic raw material or auxiliary selected from: oils, fats, waxes, film formers, surfactants, antioxidants, vitamin C, vitamin E, stabilizers, odor intensifiers, silicone oils, emulsifiers, solvents, preservatives, thickeners, rheological additives, bentonites, hectorites, silicon dioxides, Ca silicates, gelatines, high-molecular-weight carbohydrates and surface-active auxiliaries.

13. A composition according to claim 1, wherein the cosmetic active ingredient is a pyrimidinecarboxylic acid or aryl oxime.

14. A composition according to claim 1, wherein the composition is in the form of a solution, suspension, emulsion, PIT emulsions, paste, ointment, gel, cream, lotion, powder, soap, surfactant-containing cleansing preparation, oil, aerosol, spray, stick, shampoo or shower preparation.

* * * * *